US010685092B2

(12) United States Patent
Paparella et al.

(10) Patent No.: US 10,685,092 B2
(45) Date of Patent: Jun. 16, 2020

(54) EQUIPMENT FOR PROVIDING A REHABILITATION EXERCISE

(71) Applicant: TELECOM ITALIA S.p.A., Milan (IT)

(72) Inventors: Corrado Paparella, Pisa (IT); Giacomo Bartolini, Siena (IT)

(73) Assignee: TELECOM ITALIA S.p.A., Milan (IT)

( * ) Notice: Subject to any disclaimer, the term of this patent is extended or adjusted under 35 U.S.C. 154(b) by 483 days.

(21) Appl. No.: 15/512,958

(22) PCT Filed: Sep. 24, 2014

(86) PCT No.: PCT/EP2014/070329
§ 371 (c)(1),
(2) Date: Mar. 21, 2017

(87) PCT Pub. No.: WO2016/045717
PCT Pub. Date: Mar. 31, 2016

(65) Prior Publication Data
US 2017/0300663 A1    Oct. 19, 2017

(51) Int. Cl.
*G06F 19/00* (2018.01)
*A63F 13/211* (2014.01)
*A63F 13/67* (2014.01)

(52) U.S. Cl.
CPC ........ *G06F 19/3481* (2013.01); *A63F 13/211* (2014.09); *A63F 13/67* (2014.09)

(58) Field of Classification Search
CPC .................................................. A63F 2300/64
See application file for complete search history.

(56) References Cited

U.S. PATENT DOCUMENTS 5,785,630 A * 7/1998 Bobick .............. A63B 21/4034
482/4
2002/0146672 A1   10/2002 Burdea et al.
(Continued)

FOREIGN PATENT DOCUMENTS

WO    2012/139868 A1   10/2012
WO    2014/136112 A1    9/2014

OTHER PUBLICATIONS

International Search Report dated Jun. 15, 2015, in PCT/EP2014/070329, filed Sep. 24, 2014.
(Continued)

*Primary Examiner* — Reginald A Renwick
(74) *Attorney, Agent, or Firm* — Oblon, McClelland, Maier & Neustadt, L.L.P.

(57) ABSTRACT

A user equipment providing a rehabilitation exercise to a patient, the exercise including playing a videogame. The user equipment includes a processor, a display, and a motion sensing input device. The processor is configured to run the videogame, the display to show a moving target, and the device to transduce a motion of the patient into a motion of a marker on the display. The processor is configured to: before the patient starts the exercise, select a target trajectory and a maximum target speed; and, during the exercise, adjust a current target speed based on the maximum speed and a distance between the target and the marker. The patient can perform rehabilitation by playing videogames that may be remotely controlled by a therapist and whose level of difficulty may be automatically adjusted based on the patient current condition.

19 Claims, 5 Drawing Sheets

(56) References Cited

U.S. PATENT DOCUMENTS

2007/0066403 A1* 3/2007 Conkwright ............ A63F 13/10
                                                    463/43
2011/0131005 A1* 6/2011 Ueshima ............ A63B 24/0062
                                                    702/141
2013/0034837 A1   2/2013 Clapp et al.
2017/0069223 A1* 3/2017 Cramer ................ G09B 19/003

OTHER PUBLICATIONS

Gowayyed, et al., "Histogram of Oriented Displacements (HOD): Describing Trajectories of Human Joints for Action Recognition", Proceedings of the Twenty-Third International Joint Conference on Artificial Intelligence, p. 1351-1357, 2013.

* cited by examiner

EQUIPMENT FOR PROVIDING A REHABILITATION EXERCISE

TECHNICAL FIELD

The present invention relates to the field of systems and methods for rehabilitation of patients with motor and cognitive disorders. In particular, the present invention relates to a user equipment, a system and a method for providing motor and cognitive exercises for rehabilitation.

BACKGROUND ART

As known, patients that are affected by a neurodegenerative disease, such as, for instance, the Parkinson's disease, or, generally, patients experiencing motor and cognitive deficiencies spend typically long periods of time (weeks, months, years) for rehabilitation, in order to improve/recover their motor and cognitive functionalities. Often, rehabilitation may require multiple training sessions during the day.

Methods for the rehabilitation of patients affected by neurodegenerative diseases are known. Moreover, methods for rehabilitation are known which allow patients to perform training exercises at their home under the control of a therapist who interacts with the patient remotely. The therapist may remotely choose the exercises and/or the level of difficulty of the training session to be performed by the patient according to an evaluation of the patient's conditions. These methods allow reducing the workload of the therapist and the stress level of the patients, who are not forced to continually move from their house to a rehabilitation center. Moreover, the patients can be trained with exercises that are adapted to their conditions and this allows avoiding that the patients get frustrated by excessively difficult exercises or get bored by excessively easy exercises.

Moreover, rehabilitation methods are known that make use of games and videogames which typically are ad-hoc designed. These methods advantageously allow not to lose the interest and participation of the patient for rehabilitation over long periods of time.

US 2002/0146672 A1 discloses a method and system for individually exercising one or more parameters of hand movement such as range, speed, fractionation and strength in a virtual reality environment and for providing performance-based interaction with the user to increase user motivation while exercising. This method and system can be used for rehabilitation of neuromotor disorders, such as a stroke. A first input device senses position of digits of the hand of the user while the user is performing an exercise by interacting with a virtual image. A second input device provides force feedback to the user and measures position of the digits of the hand while the user is performing an exercise by interacting with a virtual image. The virtual images are updated based on targets determined for the user's performance in order to provide harder or easier exercises.

WO 2012/139868 discloses a system and methods to perform rehabilitation or physical therapy exercise while doing specifically designed video-games with the support of a therapist. Patient plays said video-games with external controllers with motion sensors connected to a PC or a laptop. The therapist can influence a gaming session of the patient by setting on a shared web-service thresholds for the patient. Said settings are gathered before starting a gaming session and patient movements are filtered by said settings to control the video-game. The patient is then limited in the movements by the feedbacks provided by the audio-visual interface of the video-game: movements on the screen are a result of the real movement done by the patient with said motion sensors filtered by the settings imposed by the therapist on the shared web space. On the other side, a patient with problems in doing some movements, can effectively play a video-game thanks to filtering imposed by the therapist. Information about the game played, and consequently about movements performed, are finally uploaded on the web-service for further analysis by the therapist.

SUMMARY OF THE INVENTION

The inventors noticed that patients affected by a neurodegenerative disease such as the Parkinson's disease may present a short-term fluctuation of their status, in particular of their movement capabilities. Indeed, within a single day, they may have conditions very similar to those of a healthy person ("on" condition or state), or, alternatively, they may show critical symptoms of the disease ("off" condition or state). These two conditions may alternate during a day at intervals of minutes or seconds. Moreover, a patient affected by the Parkinson's disease may also experience a so called "freezing" condition that is a temporary and involuntary inability to move, which may last only a few seconds.

In these cases, the therapist should constantly adjust the level of difficulty of the training exercises, in order to adapt it to the current conditions of the patient, which may be strongly variable within short periods of time. In fact, if the patient performs an exercise which is too easy or too difficult with respect to her/his present conditions, she/he may lose interest towards the rehabilitation or she/he may get frustrated, and she/he may quit. Moreover, if the patient experiences a freezing episode during an exercise, she/he will probably not be able to complete the exercise if the level of difficulty is not adjusted in real time during the exercise by the therapist. Therefore, to avoid patient's loss of interest or frustration, the workload of the therapist should be disadvantageously high, even if she/he is working remotely. Further, the therapist may realize that a number of exercises are not terminated by the patient, but disadvantageously she/he cannot be able to understand the reason that prevented the patient from carrying out the exercises.

The method of US 2002/0146672 A1, as well as the method of WO 2012/139868, disadvantageously does not allow to automatically adapt the level of difficulty of the rehabilitation exercises. For this reason, they seem not adapted to be used for rehabilitation of patients affected by a neurodegenerative disease such as the Parkinson's disease, who, as mentioned above, may experience freezing episodes.

In view of the above, the inventors have addressed the problem of providing a user equipment, a system and a method for providing motor and cognitive rehabilitation exercises to a patient (in particular, but not exclusively, to a patient with a neurodegenerative disease such as the Parkinson's disease), which allows avoiding that the patient loses interest in the rehabilitation or gets frustrated by it, without increasing the workload of the therapist.

According to the present invention, this problem is solved by a user equipment, a system and a method for providing motor and cognitive rehabilitation exercises to patients with motor and cognitive deficiencies which is automatically adaptive. In particular, adaptation provided by the present invention can be on an exercise-by-exercise basis and/or in real time (i.e. during each single exercise). The automatic adaptation provided by the present invention allows reducing the workload of the remote therapist who is not required to constantly adjust the degree and type of difficulty of the exercises performed by the patients. In this way, interactions with the patient are reduced to few control examinations and the therapist may follow more patients simultaneously.

In particular, the present invention provides a user equipment, a system and a method for providing a rehabilitation exercise based on a videogame whose level of difficulty may be automatically adjusted according to different mechanisms including: a mechanism according to which the level of difficulty is adjusted before any videogame match, and a mechanism according to which the level of difficulty is adjusted during the videogame match, on the basis of the current conditions and capabilities of the patient.

According to a first aspect, the present invention provides a user equipment for providing a rehabilitation exercise to a patient, the exercise comprising playing a videogame and the user equipment comprising a processor, a display and a motion sensing input device, wherein the processor is configured to run the videogame, the display is configured to show a target moving on the display according to the videogame, and the motion input sensing device is configured to transduce a motion of the patient into a corresponding motion of a marker on the display for tracking the target according to the videogame, the processor being further configured to:

before the patient starts the exercise, select a trajectory for the target and a maximum speed of the target; and
during the exercise, adjust a current speed of the target on the basis of the maximum speed and of a distance between the target and the marker on the display.

According to embodiments of the present invention, the processor is further configured to:
predetermine a set of trajectories;
associate each trajectory with a respective level of a trajectory parameter indicative of a complexity of the trajectory;
select a current level of the trajectory parameter; and
select the trajectory within a sub-set of the pre-determined set of trajectories, the sub-set being associated with the current level of the trajectory parameter.

According to other embodiments, the set of trajectories are predetermined by a therapist during an initial calibration phase. During this phase, the therapist may also associate each trajectory with the respective level of the trajectory parameter indicative of a complexity of the trajectory.

According to embodiments of the present invention, the processor is further configured to:
predetermine a set of maximum speed values;
associate each maximum speed value with a respective level of a speed parameter; and
select a current level of the speed parameter.

According to other embodiments, the set maximum speed values are predetermined by the therapist during the initial calibration phase. During this phase, the therapist may also associate each maximum speed value with a respective level of the speed parameter.

Preferably, the level of the trajectory parameter and the level of the speed parameter range within a discrete set of integer values.

Preferably, the videogame comprises a number of frames, and wherein the processor is further configured to compute the distance between the target and the marker and to adjust the current speed value of the target on a frame-by-frame basis.

Preferably, the processor is further configured to adjust the current speed value of the target at a frame i of the videogame by computing a target speed value $v(i)$ as a difference between the maximum speed value and the maximum speed value weighted by the distance $d(i)$ between the target and the marker at frame i and by a pre-defined maximum distance between a position of the target at frame i and a position of the marker at frame i.

Preferably, the processor is further configured to compute, at the end of each exercise, a first score on the basis of a mean distance between the target and the marker along the selected trajectory.

Profitably, the processor is further configured to evaluate, at the end of each exercise, a new level of the speed parameter as follows:
if the first score obtained by the patient is greater than an upper threshold, the new level of the speed parameter is equal to the current level of the speed parameter incremented by 1; and
if the first score obtained by the patient is lower than the upper threshold and lower than a lower threshold, the new level of the speed parameter is equal to the current level of the speed parameter decremented by 1.

Preferably, the processor is further configured to select, at the start of a new exercise, the maximum speed value by selecting a maximum speed value associated with the new level of the speed parameter.

Preferably, the processor is further configured to compute, at the end of each exercise, a second score on the basis of a distance $d\_t$ between the trajectory of the target and a trajectory of the marker.

Preferably, the distance $d\_t$ is computed by using a trajectory descriptor, wherein the trajectory descriptor is based on a histogram of oriented displacements.

Preferably, the processor is further configured to evaluate, at the end of each exercise, a new level of the trajectory parameter as follows:
if the second score obtained by the patient is greater than a further upper threshold, the new level of the trajectory parameter is equal to the current level of the trajectory parameter incremented by 1; and
if the second score obtained by the patient is lower than the further upper threshold and lower than a further lower threshold, the new level of the trajectory parameter is equal to the current level of the trajectory parameter decremented by 1.

Preferably, the processor is further configured to select, at the start of a new exercise, the trajectory by selecting a trajectory associated with the new level of the trajectory parameter.

Preferably, the processor is further configured to associate a trajectory with a level of the trajectory parameter on the basis of the value of a highest bin within a histogram of oriented displacements for the trajectory of the target.

Preferably, the processor is further configured to upload, at the end of each exercise, the first score, the new level of the speed parameter, the second score and the new level of the trajectory parameter on a server accessible by a therapist.

Preferably, the motion sensing input device comprises one or more of: a mouse, a touchscreen display, an inertial sensor, a motion controller.

According to a second aspect, the present invention provides a system for providing a rehabilitation exercise to a patient, the exercise comprising playing a videogame, the system comprising first and second user equipment and a server, the first and second user equipment being configured to connect to the server, wherein the server comprises a database configured to store data indicative of the exercise and data indicative of scores achieved by the patient in executing the exercise, wherein the first user equipment is configured to provide access to the server to a therapist for managing the data indicative of the exercise, and wherein the second user equipment comprises a processor, a display and a motion sensing input device, wherein the processor is configured to run the videogame, the display is configured to show a target moving on the display according to the videogame, and the motion input sensing device is configured to transduce a motion of the patient into a corresponding motion of a marker on the display for tracking the target according to the videogame, the processor being further configured to:

before the patient starts the exercise, select a trajectory for the target and a maximum speed of the target; and during the exercise, adjust an actual speed of the target on the basis of the maximum speed and of a distance between the target and the marker on the display.

According to a third aspect, the present invention provides a method for providing a rehabilitation exercise to a patient, the exercise comprising playing a videogame according to which a moving target is shown on a display of a user equipment of the patient, the playing the videogame comprising tracking the target on the display by the patient, the method comprising:

a) before starting the exercise, selecting a trajectory for the target and a maximum speed value of the target; and b) during the exercise, adjusting a current speed value of the target on the basis of the maximum speed value and of a distance between the target and a marker representative of a position of the patient (15) on the display.

According to a fourth aspect, the present invention provides computer program product comprising computer-executable instructions for performing, when the program is run on a computer, the steps of the method as set forth above.

BRIEF DESCRIPTION OF THE DRAWINGS

The present invention will become clearer from the following detailed description, given by way of example and not of limitation, to be read with reference to the accompanying drawings, wherein.

DETAILED DESCRIPTION OF PREFERRED EMBODIMENTS OF THE INVENTION

Figure 1:
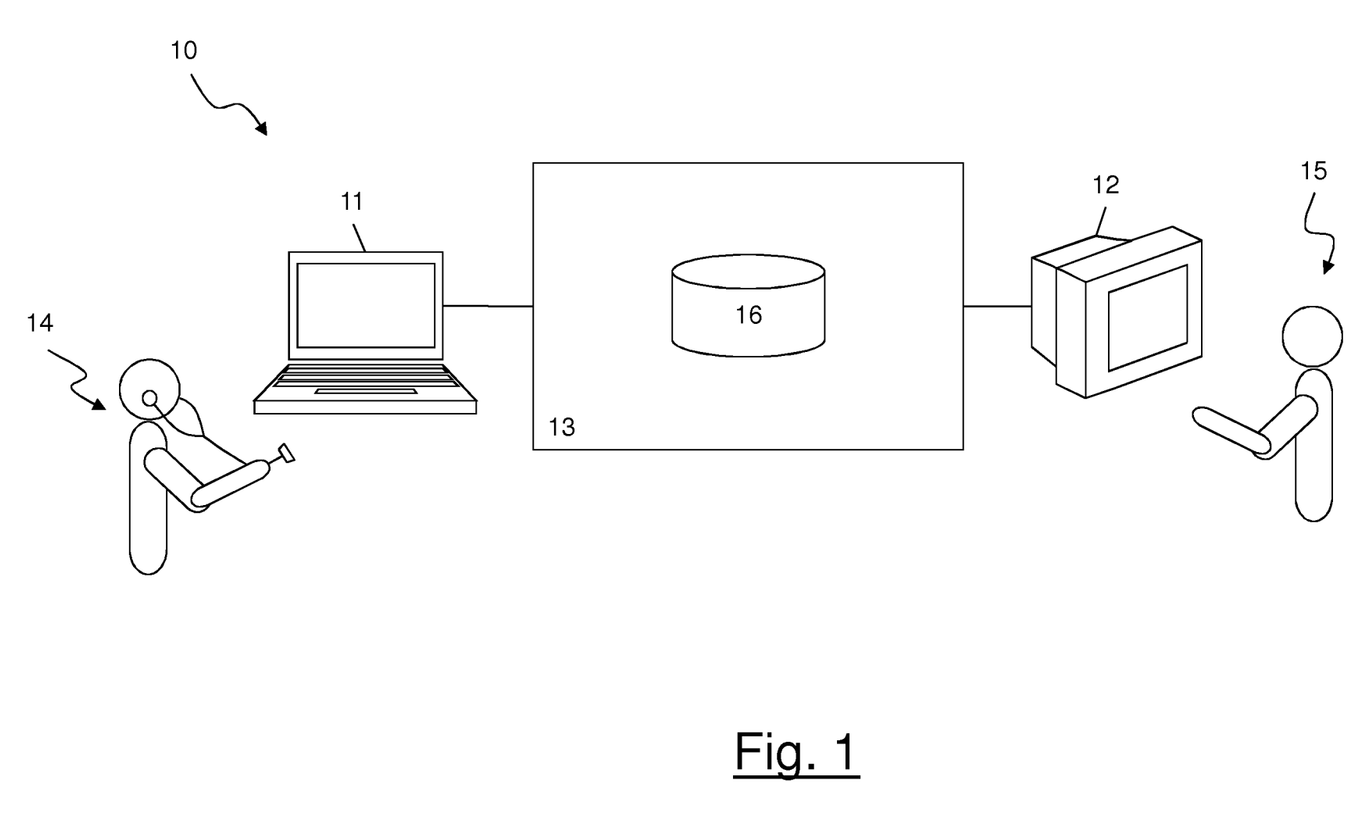
FIG. 1 is a block scheme of a system suitable for implementing the present invention.

FIG. 1 schematically shows a system 10 suitable for performing the method for providing a rehabilitation exercise according to the present invention.

The system 10 preferably comprises a first user equipment 11, a second user equipment 12 and a server 13. The first user equipment 11 and the second user equipment 12 are preferably configured to connect to the server 13 through a wired or wireless communication network. In particular, the first user equipment 11 and the second user equipment 12 are preferably configured to download and upload data from/to the server 13 through the communication network. Preferably, the first user equipment 11 and the second user equipment 12 are configured to connect to the server 13 through the Internet.

The first user equipment 11 is preferably used by a therapist 14 for remotely supporting a patient 15 in the execution of motor and cognitive exercises for rehabilitation (in the following referred to simply as "exercises") according to the method of the present invention, as it will be described herein after. In particular, the first user equipment 11 is configured to provide access to the server 13 to the therapist 14. The first user equipment 11 preferably comprises a display, a processor and an input device, such as a keyboard. The first user equipment 11 may be, for instance, a personal computer, a tablet or a smartphone.

The second user equipment 12 is preferably used by the patient 15 to execute the exercises. The second user equipment 12 may be, for instance, a personal computer (such as, for instance, an all-in-one personal computer), a tablet or a videogame console equipped with a processor, a memory (e.g. a hard-disk), a display and a motion sensing input device, i.e. a device capable of transducing a motion of the patient (in particular, a motion of a patient's hand or a patient's arm) into a corresponding motion of a marker or cursor on the display. The motion sensing input device may comprise a mouse. Alternatively or in addition, the motion sensing input device may comprise a touchscreen display. Further, the motion sensing input device may comprise, for instance, inertial sensors, that may be arranged on the hand of the patient, or a motion controller comprising an RBG camera and depth sensors, such as the Microsoft Kinect™, or the like.

The server 13 preferably comprises a database 16. The database 16 is preferably configured to store data indicative of the exercises to be performed by the patient 15 and data indicative of performance results or scores achieved by the patient 15 in performing the exercises.

Preferably, performing an exercise comprises playing a videogame.

In the following description and in the claims, the term "videogame" will indicate a task that involves human interaction with a user interface to generate visual (and, optionally, audio) feedback on a display of a user's electronic device. More in particular, the interaction may be performed though the same display on which the feedback is visualized, by using the motion sensing input device mentioned above. In particular, according to the present invention, performing an exercise preferably corresponds to playing a videogame during which a target, moving along a pre-determined trajectory, is presented to the patient 15 on the display of the second user equipment 12. Moreover, playing the videogame comprises tracking the target from the starting point of its trajectory to the end point of the same trajectory. To perform this task, the patient 15 may use the mouse of the second user equipment 12, or she/he may use the touchscreen display (in particular, the patient may track the target position with one of her/his fingers on the touchscreen display), or she/he may use another motion sensing input device among the devices mentioned above, such as the Microsoft Kinect™ (in particular, the patient may move one of her/his hands or arms in front of the Microsoft Kinect™ to track the target on the display).

According to the method of the present invention, three mechanisms for automatically (i.e. without the intervention of the therapist) adjusting the level of difficulty of an exercise according to patient's conditions and capabilities are provided.

A first mechanism comprises adjusting the maximum speed of the target between an exercise and the successive one. At the start of an exercise, the maximum speed of the target is selected among a set of pre-determined values on the basis of one or more performance indicators describing the performance of the patient during a preceding exercise.

A second mechanism comprises adjusting the trajectory of the exercise between an exercise and the successive one. At the start of an exercise, the trajectory is selected among a set of pre-determined trajectories, with different levels of difficulty, on the basis of the one or more performance indicators describing the performance of the patient during a preceding exercise. The therapist may remotely manage the trajectories by adding new trajectories to the set of trajectories available, or removing one or more trajectories, at any time between two successive training sessions comprising a number of exercises, as it will be explained herein after.

A third mechanism comprises adjusting the speed of the target in real-time during the exercise, on the basis of a current performance of the patient.

The details of implementation of the three mechanisms and the advantages thereof will be described in the following.

According to embodiments of the present invention, the server 13 preferably comprises a server application, while the second user equipment 12 preferably comprises a client application. Each application is preferably a software application. The server application is preferably a web application associated with a web site hosted at the server 13 or at another device connected to the server 13. The client application is preferably associated with a dedicated graphical user interface (GUI). The server application and the client application are preferably configured to implement a rehabilitation remote service supporting the execution of the method according to the present invention. Preferably, the therapist 14 accesses the data contained in the database 16 and interacts with the client application through the web site.

It is assumed that the patient's rehabilitation provides for performing training sessions of exercises during a given period of time. As described above, each exercise comprises playing a videogame according to which the patient should track a target moving on the display of the second user equipment 12.

During an initial calibration phase of the method of the present invention, performed before the first training session of the rehabilitation period, the therapist 14 determines a number of trajectories to be followed by the target during the exercises, and one or more difficulty parameters, each difficulty parameter being indicative of a respective degree of difficulty of an exercise.

According to a preferred embodiment of the present invention, the parameters indicative of the degree of difficulty of an exercise may comprise:
- a speed parameter indicative of a maximum speed v_max that the target can reach during the exercise; and
- a trajectory parameter indicative of a complexity of the trajectory followed by the target during the exercise.

Each difficulty parameter is preferably associated with a set of discrete integer values, or levels, ranging between a minimum value (for instance, 1) and a maximum value (for instance, 5). In particular, the speed parameter is associated with a set of speed levels sL and the trajectory parameter is associated with a set of trajectory levels tL.

Each speed level sL is associated with a given value of the maximum speed v_max, which is expressed in pixel/frame. The values of the maximum speeds associated with the speed levels are preferably determined by the therapist 14 during the initial calibration phase.

Therefore, according to the above, the speed parameter may range between 1 and 5, level 1 being indicative of a minimum level of difficulty of the exercise in term of maximum speed of the target (lowest maximum speed) and level 5 being indicative of a maximum level of difficulty of the exercise in terms of maximum speed of the target (highest maximum speed).

The trajectory parameter may range between 1 and 5, level 1 being indicative of a minimum level of difficulty of the exercise in terms of trajectory and level 5 being indicative of a maximum level of difficulty of the exercise in terms of trajectory. A level 1 trajectory may be, for instance, a simple straight trajectory. A level 5 trajectory may be for instance a complex (i.e. comprising curves) and long trajectory. These examples are not limiting. Indeed, the level of the trajectory parameter associated with a given trajectory may be based also on the conditions of the patient. For instance, a given trajectory may be associated with level 1 for a patient with a certain motor and/or cognitive disease, while the same trajectory may be associated with another level for another patient having a different motor and/or cognitive disease.

During the calibration phase the therapist 14 may also associate with each trajectory a respective trajectory level tL, on the basis of the complexity of the trajectory and conditions of the patient. Therefore, in the database 16 the trajectories determined by the therapist 14 are preferably grouped in sub-sets, each sub-set corresponding to a different trajectory level tL.

Successively, the therapist 14 preferably uploads the trajectories and the associated trajectory levels tL into the database 16 of the server 13. During the calibration phase, the therapist 14 may also upload into the database 16 the speed levels sL with the corresponding maximum speeds.

In order to upload the above data indicative of the exercises to be performed by the patient 15 into the database 16, the therapist 14 may use the first user equipment 11 and connect to the web site of the remote rehabilitation service.

According to other embodiments, each trajectory determined by the therapist during the initial calibration phase is uploaded into the database 16 by the therapist 14 and is automatically associated with a respective trajectory level tL, as it will be described in more detail herein after.

According to the present invention, each trajectory is preferably stored in the database 16 as a sequence of spatial positions referred to as points or pixels. More preferably, only a sub-set of points for each trajectory is stored in the database 16. This allows saving memory resources and also allows reducing the time for loading the videogame by the processor of the second user equipment 12, as it will be clearer herein after.

Moreover, the therapist 14 may upload into the database 16 messages addressed to the patient 15. In particular, the messages may related to instructions and advices from the therapist 14 to the patient 15 for performing the exercises.

Between two successive training sessions, the therapist 14 may also update the data contained in the database 16. In particular, the therapist 14 may add new trajectories to the set of available trajectories or modify old ones, as already mentioned in the foregoing, and she/he may upload new messages for the patient 15.

Each time the therapist 14 wishes to upload or update data into the database 16 of the server 13, she/he may use the web site.

Figure 2:
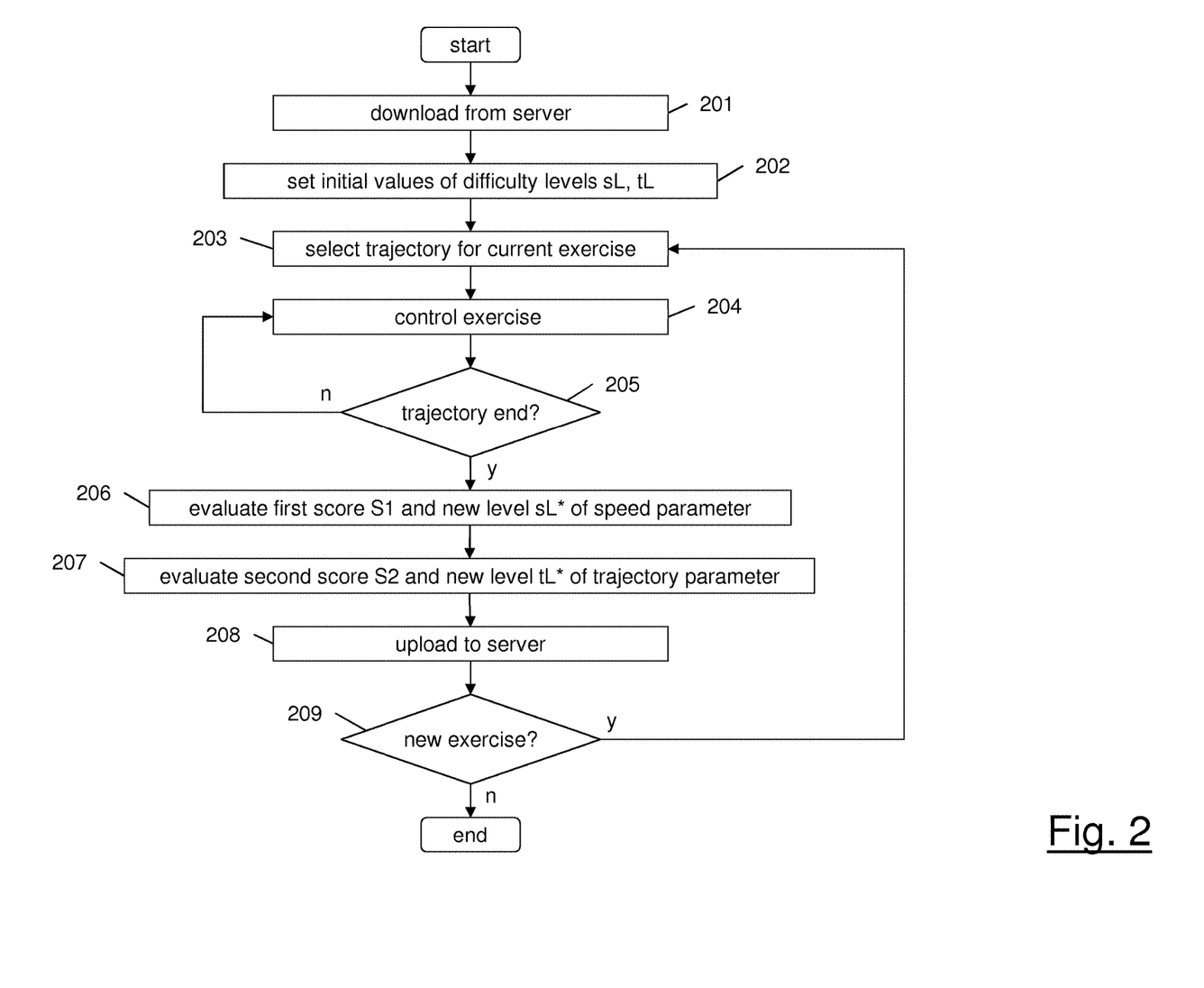
FIG. 2 is a flowchart illustrating the steps of the method according to the present invention.

With reference to FIG. 2, the steps of the method according to the present invention will be described in detail.

When the patient 15 wishes to start a training session she/he preferably operates the second user equipment 12 to launch the client application of the remote rehabilitation service (step not shown in the drawings).

The second user equipment 12, in particular the processor of the second user equipment 12, preferably connects to the server 13 (step 201). It is assumed that a connection (e.g. an Internet connection) is available for connecting the second user equipment 12 to the server 13. Upon establishment of the connection, the processor of the server 13 preferably accesses the database 16 and recovers the data indicative of the exercises to be performed by the patient 15 during the training session. In particular, if the training session is the first training session ever started by the patient 15 during his/her rehabilitation period, the processor of the server 13 preferably recovers from the database 16 the trajectories and the corresponding trajectory levels, the speed levels with the corresponding maximum speeds and possible messages from the therapist 14. Then, the processor of the server 13 preferably sends all these data to the second user equipment 12. Once downloaded from the server 13, the trajectories and the corresponding trajectory levels, the speed levels and the corresponding maximum speeds are preferably stored in the memory of the second user equipment 12.

It should be noted that each time a new training session is started at the second user equipment 12, the second user equipment 12 preferably connects to the server 13 and downloads possible new trajectories and/or new maximum speeds and/or new messages from the therapist.

At step 202, the method provides for selecting initial values of the speed level sL and the trajectory level tL at the second user equipment 12. When the first training session is started, these initial values are preferably both set to 1. Successively, at the start of a new training session, the values of the speed level sL and the trajectory level tL are set equal to the values used at the end of the preceding training session. These values are stored in the memory of the second user equipment 12, as it will be described herein after.

At step 203 the method provides for selecting a trajectory for a first exercise of the current training session on the basis of the initial value of the trajectory level tL. In particular, the trajectory for this first exercise is selected among the trajectories associated with the initial trajectory level tL and stored in the memory of the second user equipment 12. The selection of the trajectory is preferably performed in an automatic random manner by the processor of the second user equipment 12.

At this point, the display of the second user equipment 12 preferably shows a set of instructions for the patient 15 describing to her/him how to execute the first exercise. The set of instructions may be in the form of a pop-up window of the dedicated GUI. When the patient 15 is ready to start, she/he may send a corresponding command to the second user equipment 12 by, e.g., pressing a virtual button of the dedicated GUI or touching the screen of the second user equipment 12.

Upon reception of the command from the patient 15, the second user equipment 12 preferably operates its display to show a starting point of the selected trajectory and the target at a position coinciding with the starting point of the trajectory.

Then, the patient 15 may start playing the videogame by, for instance, touching the screen in correspondence of the target or at a position nearby. Alternatively, if the patient is using a mouse, she/he may start playing by positioning the mouse's cursor on the target. Furthermore, if a motion controller such as the Microsoft Kinect™ is used, the patient may start playing by placing her/himself in front of the display and moving her/his hand towards the position of the target and/or performing a predefined movement such as, for instance, opening and closing the hand.

In any case, as already mentioned above, the movement of the patient 15 is converted into the movement of a corresponding marker or cursor on the display. In particular, the marker may represent the position of the patient's finger, or the position of the mouse, or the position of the patient's hand/arm on the display, depending on the device the patient is using (i.e. a touchscreen, a mouse, a motion controller, respectively).

Herein after, the patient will be indicated also as "player".

When the marker reaches the target, the latter starts moving along the selected trajectory. At this point, the player should track the target along the trajectory by, for instance, moving her/his finger on the touchscreen display, or moving the mouse, or moving her/his hand/arm.

Figure 3:
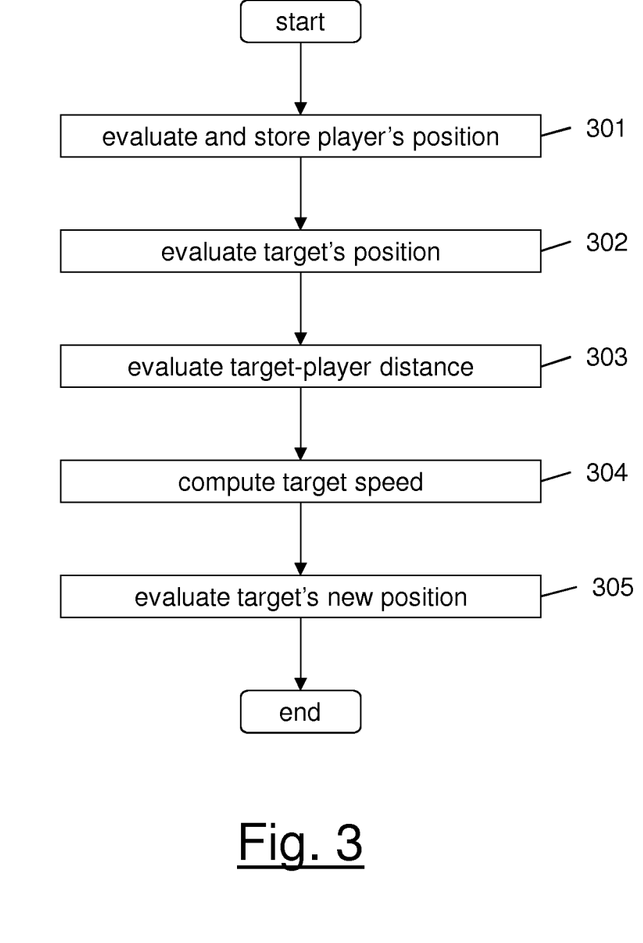
FIG. 3 is a flowchart illustrating in more detail the step of controlling an exercise performed by a patient according to embodiments of the present invention.

Then, the method provides for iteratively performing step 204 in order to control the exercise to be executed by iteratively implementing sub-steps 301-305 of the flowchart of FIG. 3. Specifically, each iteration of sub-steps 301-305 corresponds to a frame of the videogame. Sub-steps 301-305 are preferably performed by the processor of the second user equipment 12.

With reference to FIG. 3, at step 301, the current position of the marker is evaluated and it is stored into the memory of the second user equipment 12. Then, at step 302, the current position of the target is preferably evaluated. Here, the expression "current position" is referred to the position, either of the marker or of the target, on the current frame of the videogame.

It is assumed that the videogame comprises a number N of frames, so that this number also corresponds to the number of iterations of the control step 204, i.e. of the sub-steps 301-305.

At step 303, a moving distance d(i) (i being an index associated with the current frame or iteration, i=1, . . . , N) between the current position of the target and the current position of the marker is evaluated. Preferably, the moving distance d(i) may be evaluated by computing a Euclidean distance between the current position of the target and the current position of the marker.

Then, at step 303, a cumulative distance D between the target and the marker is computed. Specifically, when step 303 is performed for the first time (i=1), the cumulative distance D is preferably set equal to the moving distance d(1) evaluated at the first frame of the videogame. Successively, at each iteration of step 303 corresponding to a successive frame of the videogame (i=2, . . . , N), the cumulative distance is preferably computed by adding the moving distance d(i) computed at the current iteration i to the cumulative distance computed at the preceding iteration i−1 according to equation:

$$D(i)=D(i-1)+d(i) \quad [1]$$

where D(i) is the cumulative distance at iteration i, D(i−1) is the cumulative distance at iteration i−1 and d(i) is the moving distance at iteration i.

At step 304, a target speed is preferably computed as the difference between the maximum target speed associated with the value of the speed level sL set at step 202 and a weighted value thereof, namely the maximum speed value weighted by the moving distance d(i) computed at iteration i and by a pre-defined maximum distance between the target's position and the marker's position. In particular, the target speed is preferably computed according to the following equation:

$$v(i) = v\_max - \left(\frac{v\_max}{d\_max}\right) \cdot d(i) \qquad [2]$$

wherein v(i) is the target speed computed at iteration i, v_max is the maximum target speed associated with the value of the speed level sL set at step 202, d_max is the pre-defined maximum distance between the target's position and the marker's position, and d(i) is the moving distance computed at iteration i. It should be noted that, if the moving distance d(i) between the target's position and the marker's position reaches the maximum distance d_max, the targets stops and "waits" for the marker (this situation may happen when the patient is experiencing a freezing episode and she/he has difficulty in moving her/his hand or arm). The maximum distance d_max is preferably pre-determined by the therapist during the calibration phase on the basis of the patient's conditions: in particular, it is preferably uploaded by the therapist 14 into the database 16 of the server 13 and downloaded into the memory of the second user equipment 12 upon launching the client application, and may be updated by the therapist between any two training sessions.

The target speed v(i) and the maximum speed v_max are both expressed in pixel/frame, i.e. they are indicative of, respectively, the number of pixels that the target travels in one frame and the maximum number of pixels that the target may travel in one frame.

After having computed the target speed v(i), the processor of the second user equipment 12 preferably sets the target speed equal to the computed value v(i).

It should be noted that the method of the present invention advantageously allows adjusting in real time the target speed according to the current conditions and capabilities of the patient. Indeed, if the patient is not able to track the target (because, for instance, she/he is experiencing a freezing episode), the moving distance d(i) increases while the target speed decreases (see equation [2]). Adjusting the target speed in real-time allows the patient to complete the exercise in any condition without getting frustrated.

As it will be described in greater detail herein after, if the patient carries out the exercise by reaching the end point of the trajectory, performance indicators (or scores) are computed so as to allow the therapist to monitor the patient's performances, gather information about the patient's conditions and her/his progress in rehabilitation, and also modify the level of difficulty of the exercises, by, for instance, designing new trajectories or adjusting the speed levels sL.

On the other hand, if the patient is able to track the target, the moving distance d(i) may decrease or remain constant and the target speed may, respectively, increase or remain constant according to equation [2]. In this way, the patient does not lose interest in performing the exercise.

Again with reference to FIG. 3, at step 305, a new position of the target (corresponding to the position that the target will take at frame i+1) is preferably evaluated on the basis of the target speed v(i) computed at step 304 and of the trajectory that the target is following.

In particular, if all the points of the trajectory are stored in the database 16, the new position of the target corresponds to the point of the trajectory which is v(i) pixels forward along the trajectory with respect to the point of the trajectory corresponding to the current position of the target.

Otherwise, if, as described above, only a sub-set of points of the trajectory is stored in the database 16, the new position of the target is preferably evaluated by performing a linear interpolation between the position of the target used at step 303 to evaluate the moving distance d(i) and the point of the trajectory towards which the target shall move, this point belonging to the sub-set of points stored in the database 16 for that specific trajectory.

Specifically, by assuming that in a Cartesian coordinate system the position of the target at step 303 has coordinates (X1, Y1) and that the point of the trajectory towards which the target shall move has coordinates (X2, Y2), the coordinates (X, Y) of the position of the target at frame i+1 may be computed according to the following equations:

$$X = (1-\mu) \cdot X1 + \mu \cdot X2 \qquad [3]$$

$$Y = (1-\mu) \cdot Y1 + \mu \cdot Y2 \qquad [4]$$

where μ is a real number comprised between 0 and 1.

Provided that the target speed v(i) may be written as:

$$v(i) = \sqrt{(X-X1) + (Y-Y1)}, \qquad [5]$$

by replacing in equation [5] the expressions of X and Y derived from equations [3] and [4], the parameter μ can be computed as a function of v(i), whose value is known from step 304. Once the value of parameter μ is obtained, it may be used in equations [3] and [4] to get the new position (X, Y) of the target.

With reference again to the flowchart of FIG. 2, for each i-th frame, i=1, ..., N, the processor preferably checks (step 205) whether the target has reached the end point of the trajectory and whether the player's marker has reached the end point of the trajectory.

If the target and/or the player's marker have not reached the end point of the trajectory (branch "no" of step 205), steps 301-305 and step 205 are repeated. Iterations of steps 301-305 and 205 stop and the exercise terminates when the target and the player's marker reach the end point of the trajectory (branch "yes" of step 205).

Then, the method provides (step 206) for evaluating a first score S1 and, on the basis of the first score S1, for evaluating a new speed level sL* to be used in a next exercise that can be a successive exercise of the same training session or the first exercise of a new training session.

Successively, at step 207, the method provides for evaluating a second score S2 and, on the basis of the second score S2, for evaluating a new trajectory level tL* to be used in a next exercise that can be a successive exercise of the same training session or the first exercise of a new training session.

Steps 206 and step 207 will be described in greater detail herein after with reference to the flowcharts of FIGS. 4 and 5, respectively. Steps 206 and 207 may be performed sequentially as represented in the flowchart of FIG. 2, or they may be performed in parallel. They are preferably performed by the processor of the second user equipment 12.

At step 208, the first score S1, the second score S2, the new speed level sL* and the new trajectory level tL* are preferably uploaded from the second user equipment 12 to the server 13, and they are stored in the database 16 for being used in a successive exercise.

Once uploaded in the server, the first score S1, the second score S2, the new speed level sL* and the new trajectory level tL* may be remotely accessed by the therapist 14 for monitoring the performances of the patient 15. The remote access by the therapist 14 may be performed through the dedicated GUI at the first user equipment 11. The scores and the levels may be downloaded or simply displayed at the first user equipment 11.

At step 209, the patient 15 may choose to perform another exercise (i.e. play another videogame) or to terminate the current training session. If the patient chooses to perform another exercise, steps 203-208 are repeated. In this case, the speed level and the trajectory level for the new exercise are set equal to the values computed at step 206 and step 207, respectively, of the preceding exercise. Then, a new trajectory is selected (step 203) and a new exercise is started. The operations at steps 204-208 are exactly the same as described above.

Optionally, the method of the present invention may provide for operating the second user equipment 12 to show, on its display, encouragement messages for the patient 15. These messages may be in the form of pop-up windows, whose content depends on the obtained scores. For instance, if the patient 15 in performing a new exercise obtains a first score or a second score or both that is(are) lower than the scores obtained in a preceding exercise, a message may be shown to the patient encouraging her/him to complete the exercise. Otherwise, if the patient 15 in performing a new exercise improves her/his performances, a message may be shown with encouragement words such as "well done!", "good job!", or the like. Preferably, at the start of any new exercise a message may be shown to the patient 15 reporting to her/him the scores obtained in the exercise just terminated so that the patient can be encouraged to perform better the next exercise.

It is to be noticed that all the steps of the method according to the present invention are performed automatically after launching the videogame at the second user equipment 12, without any intervention of the therapist 14. This advantageously imply that the workload of the therapist is greatly reduced.

In the following, step 206 will be described in greater detail with reference to the flowchart of FIG. 4.

Figure 4:
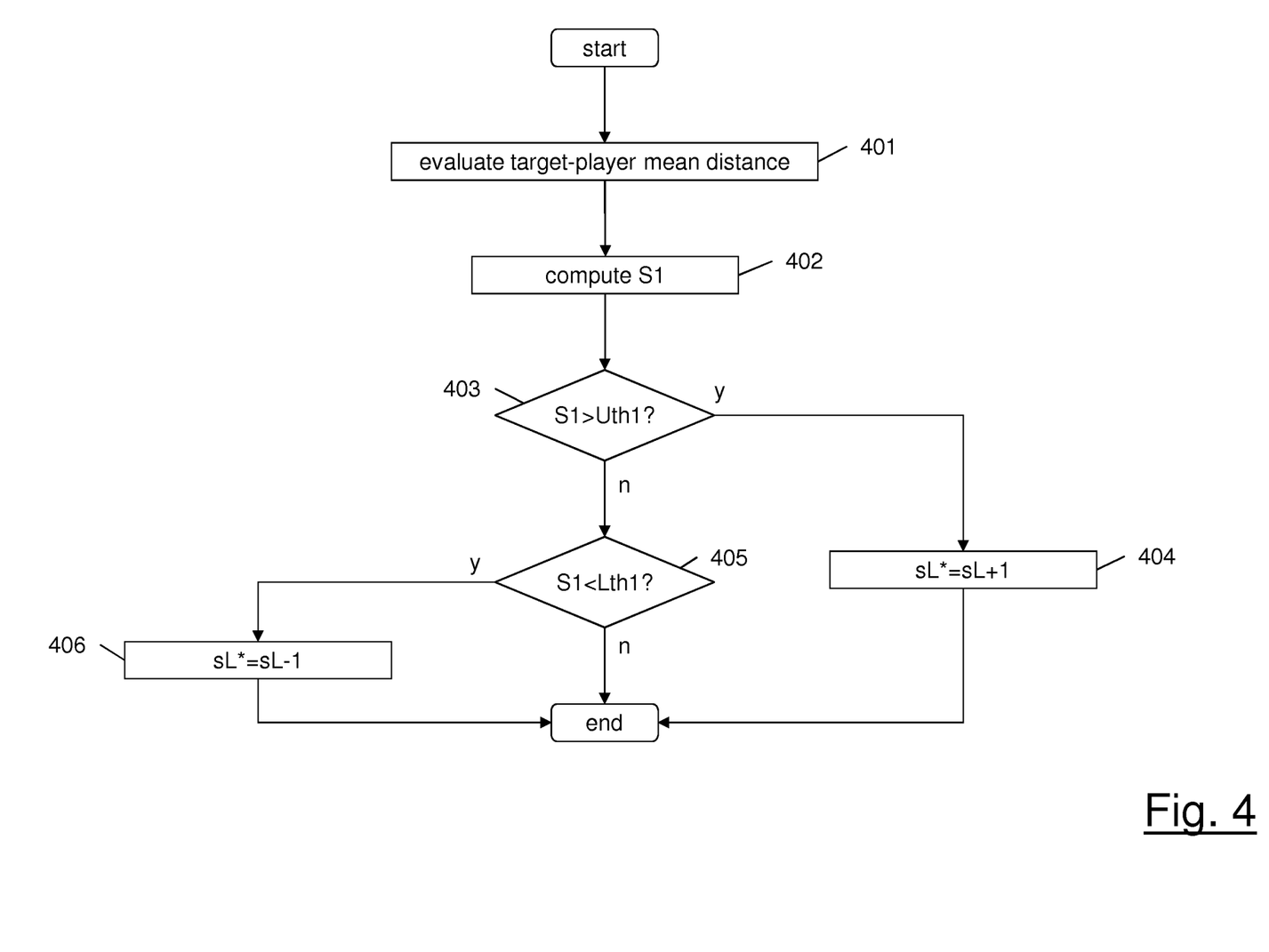
FIG. 4 is a flowchart illustrating in more detail the step of evaluating a first score and a new level of a speed parameter according to embodiments of the present invention.
Figure 5:
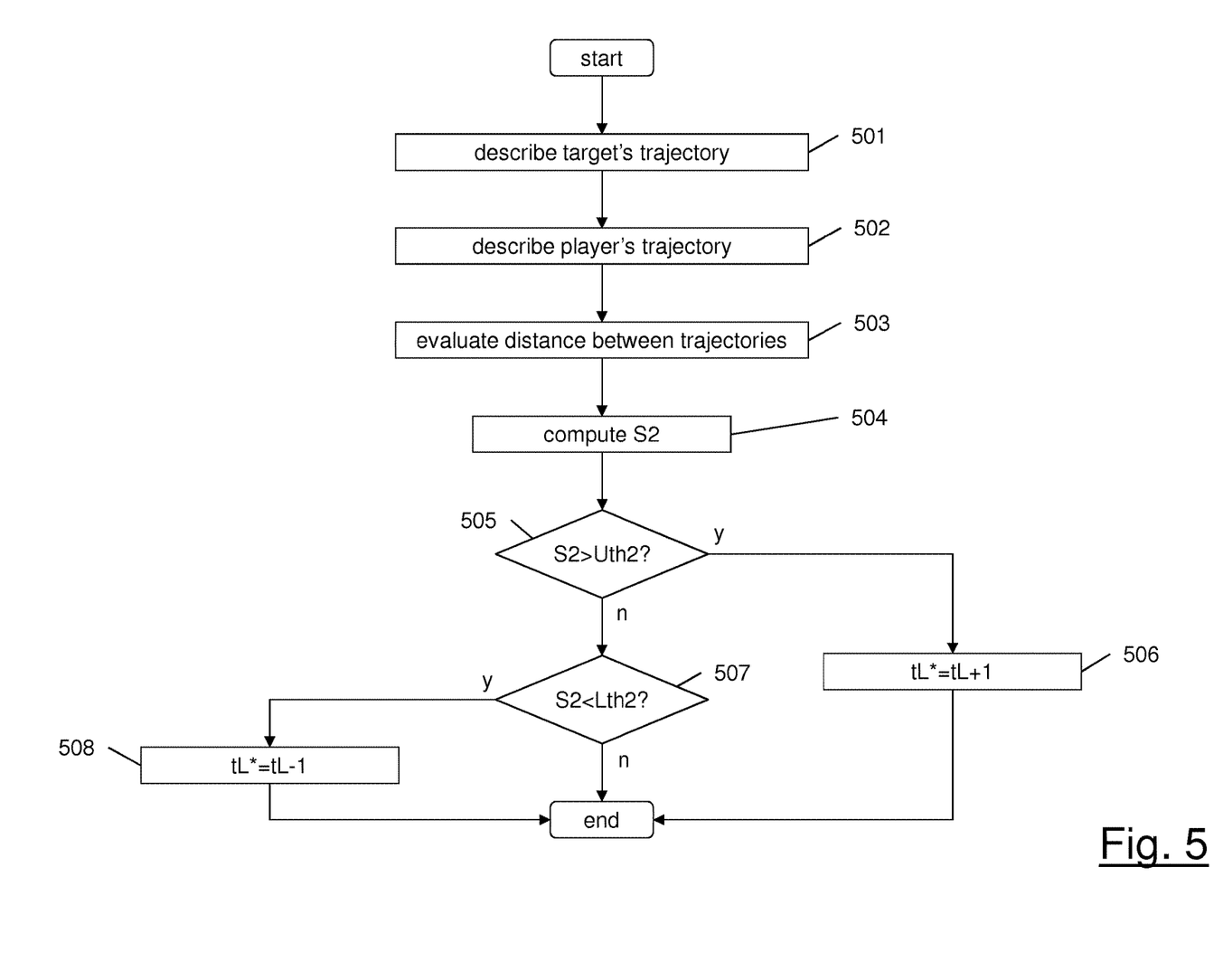
FIG. 5 is a flowchart illustrating in more detail the step of evaluating a second score and a new level of a trajectory parameter according to embodiments of the present invention.

With reference to FIG. 4, step 401 is preferably performed at the end of any exercise (branch "yes" of step 205), to compute the first score S1 representative of the capacity of the patient/player to track the target closely.

In order to compute the first score S1, a mean distance D_m between the position of the target and the position of the player's marker is preferably evaluated as:

$$D\_m = \frac{D(N)}{N} \quad [6]$$

where D_m is the mean distance, N is the number of frames of the exercise and D(N) is the cumulative distance at the end of the exercise (i.e. the cumulative distance computed according to equation [1] for the last frame of the exercise).

Then, at step 402, the mean distance D_m is preferably converted into the first score S1 by using the following equation:

$$S1 = S1\_max - \left(\frac{S1\_max}{d\_max}\right) \cdot D\_m \quad [7]$$

where S1 is the first score, S1_max is the maximum value of the first score (which is preferably a predefined integer value equal to or greater than 1), d_max is the maximum distance between the target's position and the position of the player's marker and D_m is the mean distance computed at step 401.

According to equation [7], the first score S1 may take values within the range [0÷S1_max]. For instance, if S1_max is set equal to 100, the first score S1 ranges between 0 and 100. A score range between 0 and 100 is typically used for a videogame. However, this is not limiting as also other numerical ranges may be used. Moreover, if the mean distance D_m remains greater than the maximum distance d_max, i.e. if D_m>d_max, according to equation [7], the first score S1 tends to decrease. In particular, according to equation [7], the first score S1 may become negative. However, in this case, the first score S1 is preferably set to zero.

The first score S1 is preferably used to evaluate the new speed level sL* to be used for the next exercise.

In particular, at step 403, the first score S1 is compared to an upper threshold Uth1. The upper threshold Uth1 for the first score S1 may be, for example, equal to 70.

If, the first score S1 is greater than the upper threshold Uth1, a new speed level sL* is preferably computed by incrementing by 1 the speed level sL of the exercise just ended (step 404), according to the following equation:

$$sL^* = sL + 1. \quad [8]$$

Otherwise, if the first score S1 is lower than the upper threshold Uth1, the first score S1 is preferably compared to a lower threshold Lth1 (step 405). The lower threshold Lth1 may be for example equal to 40.

If, at step 405, the first score S1 is lower than the lower threshold Lth1, a new speed level sL* is preferably computed by decrementing by 1 the speed level sL of the exercise just ended (step 406), according to the following equation:

$$sL^* = sL - 1. \quad [9]$$

If the first score S1 is greater than the lower threshold Lth1 and lower than the upper threshold Uth1, the speed level is preferably not modified.

Hence, according to the equations [8] and [9], the speed level, corresponding to the maximum speed of the target during an exercise, may be automatically adjusted exercise after exercise according to the performances of the patient that reflect her/his conditions and her/his progress in rehabilitation.

If the patient obtains a high value of the first score during an exercise, this means that she/he is able to track the target closely. Consequently, the speed of the target for the next exercise will be increased. If the patient performances improve exercise after exercise, the speed of the target may reach the highest level (for instance 5).

Otherwise, if, the patient obtains a low value of the first score during an exercise, this means that she/he is not able to track the target or she/he tracks the target loosely. Consequently, the speed of the target for the next exercise will be decreased. For example, a low value of the first score may be obtained by a patient that, during an exercise, experiences a freezing episode. If the patient performances get worse exercise after exercise, the speed of the target may reach the lowest level (for instance 1).

In the following, step 207 will be described in greater detail with reference to the flowchart of FIG. 5. As shown in FIG. 5, step 207 comprises sub-steps 501-508.

At step 207, the second score S2 is preferably computed. The second score S2 is representative of the accuracy with which the patient/player follows the trajectory of the target.

In order to compute the second score S2, the target's trajectory and the player's marker trajectory are respectively described (steps 501 and 502, respectively) by means of a trajectory descriptor that is used for describing a trajectory in terms of a set of features, such as directions, lengths, etc., and/or statistics related to such features.

According to an embodiment of the present invention, at steps 501 and 502 the descriptor used is the descriptor based on the histogram of oriented displacements (HOD) disclosed in M. A. Gowayyed et al. "Histogram of oriented displacements (HOD): describing trajectories of human joints for action recognition", Proceedings of the Twenty-Third International Joint Conference on Artificial Intelligence, Bejing (China), August 2013. According to this descriptor, the target's trajectory and the player marker's trajectory are described using a histogram of the directions between each two consecutive points, i.e. two points of the trajectory belonging to two consecutive frames. The directions are represented as angles comprised within the range 0° and 360°. Specifically, for each pair of consecutive points, the respective direction is computed as the angle comprised between the segment joining the two points and an horizontal axis of the display of the patient's user equipment 12. Then a histogram of the quantized values of the angle is created. If, for instance, the histogram comprises 8 bins, each bin represents angles spanning a 45° sector. For each angle, a specific histogram bin is determined by multiplying the angle with the length of the histogram and by dividing the obtained value by 360. The length of the segment between the two consecutive points is then added to the specific histogram bin. The sum of all the histogram bins of an histogram of oriented displacements is equal to the length of the considered trajectory. In particular, when constructing an histogram of oriented displacements, the length of the trajectory is set equal to 1 and the length of the segment between any pair of consecutive points of the trajectory is added to the respective histogram bin as a fraction of 1. In this way, each bin may have a value ranging from 0 to 1.

The highest bin represents the direction of displacement which is the most probable.

According to this embodiment of the present invention, at step 501, a first histogram of oriented displacements is determined for the trajectory of the target. At step 502, a second histogram of oriented displacements is determined for the trajectory of the player's marker. The first histogram of oriented displacements and the second histogram of oriented displacements have preferably the same number of bins.

Then, at step 503, a distance d_t between the target's trajectory and the player marker's trajectory is preferably computed as the Euclidean distance between the first histogram and the second histogram, according to the following equation:

$$d\_t = \sqrt{\sum_{j=1}^{M} (b(j) - g(j))^2} \quad [10]$$

where d_t is the trajectory distance, M is the number of bins of the histograms, b(j) is the value of the j-th bin for the target's trajectory and g(j) is the value of the j-th bin for the player's marker trajectory, wherein j=1, . . . , M.

At step 504, the trajectory distance is preferably converted into the second score S2 according to the following equation:

$$S2 = S2\_max - \left(\frac{S2\_max}{d\_max}\right) \cdot d\_t \quad [11]$$

where S2 is the second score, S2_max is the maximum value of the second score (which is preferably an integer value equal to or greater than 1), d_max is the maximum distance between the target's position and the position of the player's marker and d_t is the trajectory distance computed at step 503. According to equation [11], the second score S2 may take values within the range [0÷S2_max]. For instance, S2_max may be set equal to 100, so that the second score S2 may range, for instance, between 0 and 100.

It will be appreciated that computing the trajectory distance d_t as described above advantageously allows to highlight movements of the player in directions that are not correlated with the directions of the target trajectory (random directions). These movements may be caused by tremor of the patient's hand, which is a symptom of several neurodegenerative diseases. If the patient has a tremor, the direction of displacement between a point and the successive one is probably different with respect to the direction of the target's trajectory. If, for instance, the target's trajectory is a straight horizontal line, the patient experiencing a tremor probably has involuntary movements of the hand in a vertical direction. In this case, the histogram of oriented displacements for the trajectory of the player's marker probably comprises not only one bin whose value is equal to one, but a number of bins having values different from zero related to different directions. Therefore, the distance d_t between the target's trajectory and the player marker's trajectory is different from zero.

Moreover, using the histogram of oriented displacements for describing the trajectory advantageously allows to automatically classify the trajectory on the basis of its complexity. This classification may be used for automatically setting the trajectory level tL of a trajectory every time a new trajectory is uploaded into the server.

Indeed, the complexity of a trajectory may be represented by a parameter 1−b_max where b_max is the value of the highest bin within the histogram of oriented displacements describing the trajectory. A b_max having a value close to 1 indicates that the trajectory has a preferred direction, for instance it is straight. In this case, the trajectory may be classified as "simple" and may be associated to a low trajectory level tL, for instance 1 or 2. Otherwise, if b_max has a value not close to 1, this indicates that a preferred direction cannot be identified for the trajectory. In this case the trajectory may have a high degree of complexity, may be classified as "difficult" and it may be associated to a high trajectory level tL, for instance 4 or 5.

The second score S2 is preferably used to evaluate the new trajectory level tL* to be used for the next exercise.

In particular, at step 505, the second score S2 is preferably compared to an upper threshold Uth2. The upper threshold Uth2 for the second score S2 may be equal to, for instance, 70.

If the first score S2 is greater than the upper threshold Uth2, the new trajectory level tL* is preferably computed by incrementing by 1 the trajectory level tL of the exercise just ended (step 506), according to the following equation:

$$tL^* = tL + 1. \qquad [12]$$

Otherwise, if the second score S2 is lower than the upper threshold Uth2, the second score S2 is preferably compared to a lower threshold Lth2 (step 507). The lower threshold Lth2 may be equal to, for instance, 40.

If the second score S2 is lower than the lower threshold Lth2, the new trajectory level tL* is preferably computed by decrementing by 1 the trajectory level tL of the exercise just ended (step 508), according to the following equation:

$$tL^* = tL - 1. \qquad [13]$$

Hence, according to equations [12] and [13], the trajectory level, that indicates the level of difficulty of a current trajectory may be automatically adjusted exercise after exercise according to the performances of the patient, which reflect her/his conditions and her/his progress in rehabilitation.

If the patient obtains a high value of the second score during an exercise, this means that she/he is able to accurately follow the target's trajectory and the level of difficulty of the trajectory will be increased for the next exercise. Exercise after exercise, if the patient performances improve, the level of difficulty of the trajectory may reach the highest value, for instance 5.

Otherwise, if the patient obtains a low value of the second score during an exercise, this means that she/he is not able to follow the target's trajectory and the level of difficulty of the trajectory will be decreased for the next exercise. A low value of the second score S2 may be obtained by a patient that, during an exercise, experienced some tremors of her/his hand, causing the player's marker to go in different directions with respect to the target. Exercise after exercise, if the patient performances get worse, the level of difficulty of the trajectory may reach the lowest value, for instance 1.

Moreover, exercise after exercise, by monitoring the scores obtained by the patient, the therapist may advantageously identify critical conditions of him/her. Indeed, at the end of an exercise, if a patient has obtained a high first score and a very low second score (e.g. S2<30 within the exemplary range 0-100 mentioned above), the therapist may infer that the patient has experienced a motor disease, such as a critical tremor of his/her hand during the exercise. Indeed, she/he was able to track closely the target (high value of the first score) but she/he was not able to follow the target's trajectory because the hand moved in different directions as a result of the tremor. If the patient has obtained a high first score and a "relatively" low second score (e.g. S2<60), the cause may be that the trajectory had too many direction changes and it was too complex for the patient.

On the other hand, if at the end of an exercise, a patient has obtained a very low first score (e.g. S1<30) and a high second score, the therapist may infer that the patient has experienced a freezing episode during the execution of the exercise. Indeed, she/he was able to precisely follow the target, but at a great mean distance. This means that, during the execution of the exercise, the speed of the players' marker is decreased or that the players' marker has stopped moving. If, the patient has obtained a "relatively" low first score (S1<60) and a high second score, the target speed might be too high with respect to the ability of the patient to follow the target.

As it is clear from the above, advantageously, the method of the present invention is able to avoid that the patient loses interest in the rehabilitation process or gets frustrated by it because, according to the present invention, the patient can perform his/her rehabilitation by playing videogames that may be remotely controlled by the therapist and whose level of difficulty may be automatically adjusted on the basis of the current condition of the patient. In particular, as already mentioned above, the automatic adjustment of the maximum speed of the target and the automatic adjustment of the trajectory between two successive exercises allow providing the patient with exercises that are adapted to her/his current conditions. Moreover, the real-time adjustment of the speed of the target allows the patient to track the target and carry out the exercise in any condition. In this way, the patient will not get frustrated and will maintain a high level of participation in performing the rehabilitation exercises.

Further, the therapist has a reduced workload because the level of difficulty of the exercises can be adjusted automatically without any intervention by her/him. At the same time, by using the method of the present invention the therapist is always able to gather information about the current conditions of the patients. In particular, the therapist may understand when a patient is experiencing critical conditions such as a freezing episode or tremors and whether the patient conditions are improved or not at the end of a rehabilitation period.

The invention claimed is:

1. A user equipment for providing a rehabilitation exercise to a patient, the exercise including playing a videogame and the user equipment comprising:
   a processor;
   a display; and
   a motion sensing input device;
   wherein the processor is configured to run the videogame, the display is configured to show a target moving on the display according to the videogame, and the motion input sensing device is configured to transduce a motion of the patient into a corresponding motion of a marker on the display for tracking the target according to the videogame,
   the processor further configured to:
      before the patient starts the exercise, select a trajectory for the target and a maximum speed of the target; and
      during the exercise, adjust a current speed of the target based on the maximum speed and a distance between the target and the marker on the display,
   wherein in the selection of the trajectory the processor is further configured to
      predetermine a set of trajectories;
      associate each trajectory with a respective level of a trajectory parameter indicative of a complexity of the trajectory;
      select a current level of the trajectory parameter; and
      select the trajectory within a sub-set of the pre-determined set of trajectories, the sub-set being associated with the current level of the trajectory parameter.

2. The user equipment according to claim 1, wherein the processor is further configured to:
   predetermine a set of maximum speed values;
   associate each maximum speed value with a respective level of a speed parameter; and
   select a current level of the speed parameter.

3. The user equipment according to claim 2, wherein the level of the trajectory parameter and the level of the speed parameter range within a discrete Set of integer values.

4. The user equipment according to claim 1, wherein the videogame comprises a number of frames, and Wherein the processor is further configured to compute distance between the target and the marker and to adjust a current speed value of the target on a frame-by-frame basis.

5. The user equipment according to claim 4, Wherein the processor is further configured to adjust the current speed value of the target at a frame i of the videogame by computing a target speed value as a difference between maximum speed value and maximum speed value weighted by the distance between the target and the marker at frame i and by a pre-defined maximum distance between a position of the target at frame i and a position of the marker at frame i.

6. The user equipment according to claim 2, wherein the processor is further configured to compute, at an end of each exercise, a first score based on a mean distance between the target and the marker along the selected trajectory.

7. The user equipment according to claim 6, wherein the processor is further configured to evaluate, at an end of each exercise, a new level of the speed parameter as follows:
if the first score obtained by the patient is greater than an upper threshold, the new level of the speed parameter is equal to the current level of the speed parameter incremented by 1; and
if the first score obtained by the patient is lower than the upper threshold and lower than a lower threshold, the new level of the speed parameter is equal to the current level of the speed parameter decremented by 1.

8. The user equipment according to claim 7, wherein the processor is further configured to select, at a start of a new exercise, the maximum speed value by selecting a maximum speed value associated with the new level of the speed parameter.

9. The user equipment according to claim 7, wherein the processor is further configured to compute, at an end of each exercise, a second score based on a distance between the trajectory of the target and a trajectory of the marker.

10. The user equipment according to claim 9, wherein the distance is computed by using a trajectory descriptor, wherein the trajectory descriptor is based on a histogram of oriented displacements.

11. The user equipment according to claim 9, wherein the processor is further configured to evaluate, at an end of each exercise, a new level of the trajectory parameter as follows:
if the second score obtained by the patient is greater than a further upper threshold, the new level of the trajectory parameter is equal to the current level of the trajectory parameter incremented by 1; and
if the second score obtained by the patient is lower than the further upper threshold and lower than a further lower threshold, the new level of the trajectory parameter is equal to the current level of the trajectory parameter decremented by 1.

12. The user equipment according to claim 11, wherein the processor is further configured to select, at a start of a new exercise, the trajectory by selecting a trajectory associated with the new level of the trajectory parameter.

13. The user equipment according to claim 11, wherein the processor is further configured to upload, at the end of each exercise, the first score, the new level of the speed parameter, the second score, and the new level of the trajectory parameter on a server accessible by a therapist.

14. The user equipment according to claim 1, wherein the processor is further configured to associate a trajectory with a level of the trajectory parameter based on a value of a highest bin within a histogram of oriented displacements for the trajectory.

15. The user equipment according to according to claim 1, Wherein the motion sensing input device comprises one or more of: a mouse, a touchscreen display, an inertial sensor, a motion controller.

16. The user equipment according to claim 1, wherein during the exercise, the processor is further configured to cause the target to wait for the marker in response to the distance between the target and the marker exceeding a predetermined threshold.

17. A system for providing a rehabilitation exercise to a patient, the exercise including playing a videogame, the system comprising:
first and second user equipment and a server, the first and second user equipment being configured to connect to the server;
wherein the server comprises a database configured to store data indicative of the exercise and data indicative of scores achieved by the patient in executing the exercise;
wherein the first user equipment is configured to provide access to the server to a therapist for managing the data indicative of the exercise; and
wherein the second user equipment comprises a processor, a display, and a motion sensing input device, wherein the processor is configured to run the videogame, the display is configured to show a target moving on the display according to the videogame, and the motion input sensing device is configured to transduce a motion of the patient into a corresponding motion of a marker on the display for tracking the target according to the videogame, the processor being further configured to:
before the patient starts the exercise, select a trajectory for the target and a maximum speed of the target;
during the exercise, adjust an actual speed of the target based on the maximum speed and of a distance between the target and the marker on the display,
wherein in the selection of the trajectory the processor is further configured to
predetermine a set of trajectories;
associate each trajectory with a respective level of a trajectory parameter indicative of a complexity of the trajectory;
select a current level of the trajectory parameter; and
select the trajectory within a sub-set of the pre-determined set of trajectories, the sub-set being associated with the current level of the trajectory parameter.

18. A method for providing a rehabilitation exercise to a patient, the exercise including playing a videogame according to which a moving target is shown on a display of a user equipment of the patient, the playing the videogame including tracking the target on the display by the patient, the method comprising:
before starting the exercise, selecting a trajectory for the target and a maximum speed value of the target;
during the exercise, adjusting a current speed value of the target based on the maximum speed value and a distance between the target and a marker representative of a position of the patient on the display,
wherein selecting the trajectory includes
predetermining a set of trajectories;

associating each trajectory with a respective level of a trajectory parameter indicative of a complexity of the trajectory;

selecting a current level of the trajectory parameter; and selecting the trajectory within a sub-set of the pre-determined set of trajectories, the sub-set being associated with, the current level of the trajectory parameter.

19. A non-transitory computer readable medium storing a computer program product comprising computer-executable instructions for performing, when the program is run on a computer, the method according to claim 18.

* * * * *